(12) United States Patent
Kusunose et al.

(10) Patent No.: US 7,548,309 B2
(45) Date of Patent: Jun. 16, 2009

(54) INSPECTION APPARATUS, INSPECTION METHOD, AND MANUFACTURING METHOD OF PATTERN SUBSTRATE

(75) Inventors: Haruhiko Kusunose, Kanagawa (JP); Tomoya Tamura, Kanagawa (JP)

(73) Assignee: Lasertec Corporation, Kanagawa (JP)

( * ) Notice: Subject to any disclaimer, the term of this patent is extended or adjusted under 35 U.S.C. 154(b) by 0 days.

(21) Appl. No.: 12/025,521

(22) Filed: Feb. 4, 2008

(65) Prior Publication Data

US 2008/0192238 A1    Aug. 14, 2008

(30) Foreign Application Priority Data

Feb. 9, 2007    (JP) .............................. 2007-029958

(51) Int. Cl.
*G01N 21/88* (2006.01)
(52) U.S. Cl. .............. 356/237.2; 356/237.1; 356/237.5; 356/394
(58) Field of Classification Search ... 356/237.1–237.6, 356/394; 250/237, 559.42, 559.48, 559.39, 250/559.46
See application file for complete search history.

(56) References Cited

U.S. PATENT DOCUMENTS

| | | | | |
|---|---|---|---|---|
| 5,448,350 A | * | 9/1995 | Kohno | ..................... 356/237.2 |
| 5,528,360 A | * | 6/1996 | Kohno | ..................... 356/237.5 |
| 5,629,786 A | * | 5/1997 | Ogura et al. | ................. 349/123 |
| 5,822,055 A | * | 10/1998 | Tsai et al. | ................. 356/237.1 |
| 6,064,484 A | * | 5/2000 | Kobayashi et al. | .......... 356/390 |
| 6,365,425 B1 | * | 4/2002 | Ikota et al. | ..................... 438/16 |
| 6,800,859 B1 | * | 10/2004 | Yoshida et al. | .............. 250/372 |
| 7,274,444 B2 | * | 9/2007 | Furman et al. | ........... 356/237.2 |

FOREIGN PATENT DOCUMENTS

| | | |
|---|---|---|
| JP | 2003-4654 A | 1/2003 |
| JP | 2004-163198 A | 6/2004 |
| JP | 2006-125967 A | 5/2006 |

* cited by examiner

*Primary Examiner*—Sang Nguyen
(74) *Attorney, Agent, or Firm*—Sughrue Mion, PLLC

(57) ABSTRACT

A defect inspection apparatus according to an aspect of the present invention includes a laser source generating light beam, an objective lens focusing the light beam emitted from the laser source to form a light spot on a surface of a sample W, a prism dividing the light beam reflected from the sample into two light beams, two light receiving elements receiving the light beams divided by the prism to output output signals based on the beam amount of the received beams, and a real defect determination part determining a candidate detect as a real defect when output signals from the two light receiving elements are detected substantially at the same time.

16 Claims, 12 Drawing Sheets

RELATED ART

INSPECTION APPARATUS, INSPECTION METHOD, AND MANUFACTURING METHOD OF PATTERN SUBSTRATE

BACKGROUND OF THE INVENTION

1. Field of the Invention

The present invention relates to an inspection apparatus, an inspection method, and a manufacturing method of a pattern substrate, and more particularly, to an inspection apparatus, an inspection method, and a manufacturing method of a pattern substrate using an optical scanning.

2. Description of Related Art

A defect inspection apparatus detecting surface defect of a semiconductor wafer, a mask blank, or a photo mask or the like has recently been used in order to improve manufacturing yield of a semiconductor device. In the defect inspection apparatus, there has been a strong demand for performing the inspection with high accuracy in high spatial resolution along with the increasing miniaturization of LSIs.

As the defect inspection apparatus detecting such a micro defect, the defect inspection apparatus employing a confocal optical system has been known (Japanese Unexamined Patent Application Publication No. 2003-4654). FIG. 8 is a diagram showing a conventional inspection apparatus employing a confocal optical system. As shown in FIG. 8, a light beam emitted from a laser source 1 is made incident on an objective lens 3 through a half mirror 2 which functions as a beam splitter. The objective lens 3 focuses the incident light beam into a micro spot beam and projects the micro spot beam on a sample 7 provided on a stage 8. The reflected beam from the surface of the sample 7 is reflected by the half mirror 2 to be made incident on a light receiving element 6a of a photodetector 6 through a relay lens 5 and a spatial filter 9 having a pin hole 9a.

In the confocal optical system, the beam reflected from the sample surface provided in a focal position of the objective lens 3 can transmit the pin hole 9a whereas the reflected beam from the sample surface which is deviated from the focal position cannot transmit the pin hole 9a, which decreases the output signal intensity of the photodetector 6. Therefore, the defect of the sample surface can be detected from the output signal intensity from the photodetector 6. Further, a light blocking plate 4 is provided on an optical path of the light beam reflected by the half mirror 2. The light blocking plate 4 blocks half of the light on one side in a direction corresponding to a scan direction of the light spot on the surface of the sample 7. Hence, it is possible to change beam amount that is made incident on the light receiving element 6a depending on a defect shape to detect the defect shape.

However, these defect inspection apparatus cause problems as follows. The half of the detection light is blocked in the conventional defect inspection apparatus, which causes loss of intensity of the output signal generated by receiving the detection light. Therefore, the output signal is susceptible to shot noise or thermal noise. In the typical defect inspection of a semiconductor wafer, the generated output signal is compared with positive/negative limit value (slice level). When the comparison result exceeds the slice level, it is determined that there is a defect. Therefore, false detect is often generated in the conventional technique. False detection is occurred when there is no real defect but the output signal exceeds the slice level due to noise. When the slice level is made lower in order to improve the detection sensitivity against the real defect, probability of occurring the false detect is increased, which means it is difficult to improve the detection sensitivity against the real defect. Further, when the intensity of the beam which is made incident on the defect is fluctuated by the noise or the like to generate top/bottom asymmetric signal, the detection accuracy degrades.

To overcome the above-described problem, we suggested the inspection apparatus in which the light spot focused on the sample scans the region where the light spot overlaps the light spot of the adjacent scan line so as to illuminate the region (Japanese Unexamined Patent Application Publication No. 2006-125967). In such an inspection apparatus, it is determined whether there is a defect candidate detected by light spots a and b that are adjacent to each other within a certain distance as shown in FIG. 10. Then the false defect is eliminated and only the real defect is detected.

However, in the conventional inspection apparatus, it is impossible to perform high-speed inspection since the light spot focused on the sample scans the region where the light spot overlaps the light spot of the adjacent scan line so as to illuminate the region.

Further, the beam profile of the light beam that is emitted from the laser source typically shows a normal distribution characteristic having a peak at the center. Therefore, the detection sensitivity of the defect degrades as the position of the defect is away from the center of the light spot focused on the sample. As shown in FIG. 11, even when the defect is positioned at the center of a light spot a, this defect is positioned at the edge of an adjacent light spot b, which means the detection sensitivity by the light spot b degrades. The problem as stated is also caused even in the surface inspection other than the semiconductor wafer such as defect detection of mask blank for manufacturing a semiconductor device.

The present invention has been made in view of the above circumstances. One object of the present invention is to provide an inspection apparatus, an inspection method, and a manufacturing method of a pattern substrate that are able to perform inspection with fewer loss of the signal intensity, with high detection sensitivity, and with high speed.

SUMMARY OF THE INVENTION

According to a first aspect of the present invention, there is provided an inspection apparatus including a light source generating light beam, a lens focusing the light beam emitted from the light source to form a light spot on a sample surface, an optical dividing element dividing the light beam reflected from the sample surface or transmitted through the sample into a plurality of different light beams, a first photodetector receiving a first light beam divided by the optical dividing element to output a first output signal based on a beam amount of the received beam, a second photodetector receiving a second light beam divided by the optical dividing element to output a second output signal based on a beam amount of the received beam, a defect candidate detection part detecting a defect candidate based on the first output signal and the second output signal to output a first defect candidate signal and a second defect candidate signal, and a real defect determination part determining the defect candidate as a real defect upon detecting the first defect candidate signal and the second defect candidate signal within a certain period of time. This makes it is possible to perform defect inspection with high detection sensitivity and with high speed.

According to the inspection apparatus of a second aspect of the present invention, the real defect determination part determines that the defect candidate is the real defect when the first defect candidate signal and the second defect candidate signal are detected substantially at the same time. This makes it possible to perform the defect detection with high precision.

The inspection apparatus according to a third aspect of the present invention further includes a circuit increasing pulse widths of the first defect candidate signal and the second defect candidate signal, in which the real defect determination part determines that the defect candidate is the real defect when the first defect candidate signal and the second defect candidate signal whose pulse widths are increased are detected substantially at the same time. This makes it possible to perform the defect inspection with high detection sensitivity.

The inspection apparatus according to a fourth aspect of the present invention further includes a scan part scanning relative positions of the sample and the light spot along a scan line, in which the scan part scans a region where the light spot overlaps the light spot of an adjacent scan line so as to illuminate the region. This makes it possible to perform the defect inspection with higher precision.

According to the inspection apparatus of a fifth aspect of the present invention, the optical dividing element is disposed at a position indicating substantially half of the optical path of the light beam reflected from the region having no defect on the sample, the optical dividing element divides the light beam by changing propagation direction of the light beam which is made incident on the optical dividing element.

According to the inspection apparatus of a sixth aspect of the present invention, the optical dividing element is a prism disposed on the optical path of the light beam reflected from the sample.

The inspection apparatus according to a seventh aspect of the present invention further includes a circuit calculating a difference signal based on the first output signal and the second output signal, and a first comparing circuit comparing the difference signal with a slice level, in which a defect type of the sample is identified based on the comparing result of the first comparing circuit. This makes it possible to determine whether the defect type is convex or concave more precisely.

The inspection apparatus according to an eighth aspect of the present invention further includes a circuit calculating a sum signal based on the first output signal and the second output signal, and a second comparing circuit comparing the sum signal with a slice level, in which a defect type of the sample is identified based on the comparing result of the second comparing circuit. This makes it possible to precisely determine whether the defect type is spot-type defect or not.

The inspection apparatus according to a ninth aspect of the present invention further includes a diffraction grating converting the light beam emitted from the light source into a plurality of light beams. This makes it possible to perform the defect inspection with higher speed.

The inspection apparatus according to a tenth aspect of the present invention includes a plurality of light sources. This makes it possible to perform the defect inspection with higher speed.

According to an eleventh aspect of the present invention, there is provided an inspection method inspecting a defect of a sample using a light beam including a step for forming a light spot on a sample surface by focusing the light beam to illuminate the light spot on the sample, a step for relatively moving the light spot and the sample to scan the sample surface by the light spot, a step for dividing the light beam reflected from the sample surface or transmitted through the sample into a first light beam and a second light beam, a step for detecting a first defect candidate signal from a first output signal based on a beam amount of the first light beam, a step for detecting a second defect candidate signal from a second output signal based on a beam amount of the second light beam, and a step for determining a defect candidate as a real defect upon detecting the first defect candidate signal and the second defect candidate signal within a certain period of time. This makes it possible to perform the defect inspection with high detection sensitivity and with high speed.

According to the inspection method according to a twelfth aspect of the present invention, the defect candidate is determined as the real defect when the first defect candidate signal and the second defect candidate signal are detected substantially at the same time. This makes it possible to perform the defect inspection with high precision.

The inspection method according to a thirteenth aspect of the present invention includes a step for increasing pulse widths of the first defect candidate signal and the second defect candidate signal, in which the defect candidate is determined as the real defect when the first defect candidate signal and the second defect candidate signal whose pulse widths are increased are detected substantially at the same time. This makes it possible to perform the defect inspection with high detection sensitivity.

The inspection method according to a fourteenth aspect of the present invention includes a step for scanning a region where the light spot overlaps the light spot of an adjacent scan line so as to illuminate the region. This makes it possible to perform the defect inspection with high precision.

According to the inspection method of a fifteenth aspect of the present invention, the step for dividing the light beam reflected from the sample into the first light beam and the second light beam divides the light beam reflected from the region having no defect on the sample into substantially in half.

The inspection method according to a sixteenth aspect of the present invention includes a step for calculating a difference signal based on the first output signal and the second output signal, and a step for comparing the difference signal with a slice level to identify a defect type of the sample based on the comparing result. This makes it possible to determine whether the type of defect is the convex defect or the concave defect more precisely.

The inspection method according to a seventeenth aspect of the present invention includes a step for calculating a sum signal based on the first output signal and the second output signal, and a step for comparing the sum signal with a slice level to identify a defect type of the sample based on the comparing result. This makes it possible to precisely determine whether the type of defect is the spot-type defect or not.

According to an eighteenth aspect of the present invention, there is provided a manufacturing method of a pattern substrate including: a step for detecting a defect of a substrate using the inspection method described above, the substrate being a sample, a step for modifying the detected defect, and a step for forming a pattern on the substrate whose defect is modified. This makes it possible to detect the defect on the substrate with high detection sensitivity and to improve manufacturing yield.

According to the present invention, it is possible to provide the inspection apparatus, the inspection method, and the manufacturing method of the pattern substrate that are able to perform defect inspection with high detection sensitivity and with high speed.

The above and other objects, features and advantages of the present invention will become more fully understood from the detailed description given hereinbelow and the accompanying drawings which are given by way of illustration only, and thus are not to be considered as limiting the present invention.

DESCRIPTION OF THE PREFERRED EMBODIMENTS

The embodiments of the present invention will now be described with reference to the drawings. The description is made below for the purpose of showing the preferred embodiments of the present invention. The scope of the present invention is not limited to the embodiments shown below. In the description below, the components to which the same reference symbols are given show the same components.

Figure 1:
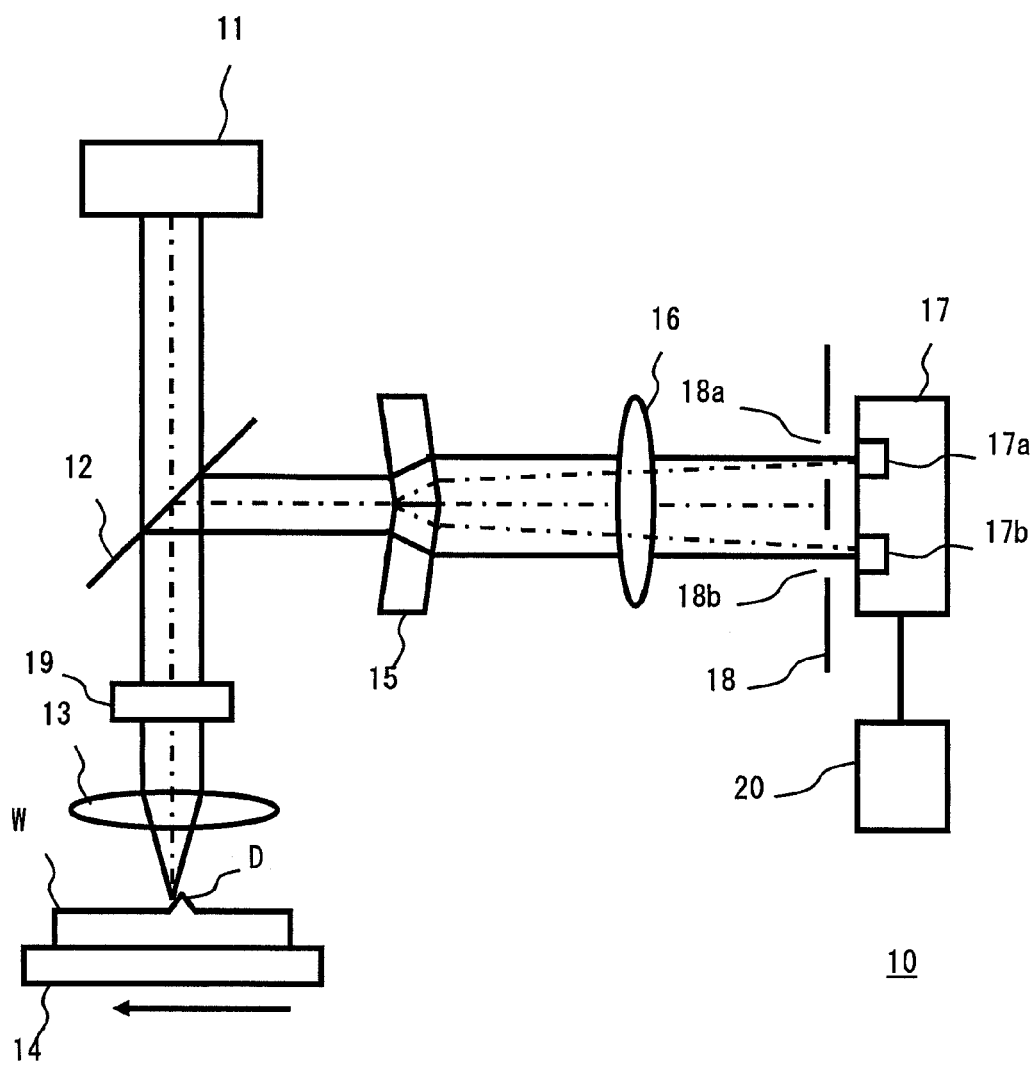
FIG. 1 shows an example of a configuration of a defect inspection apparatus according to the embodiment.
Figure 2:
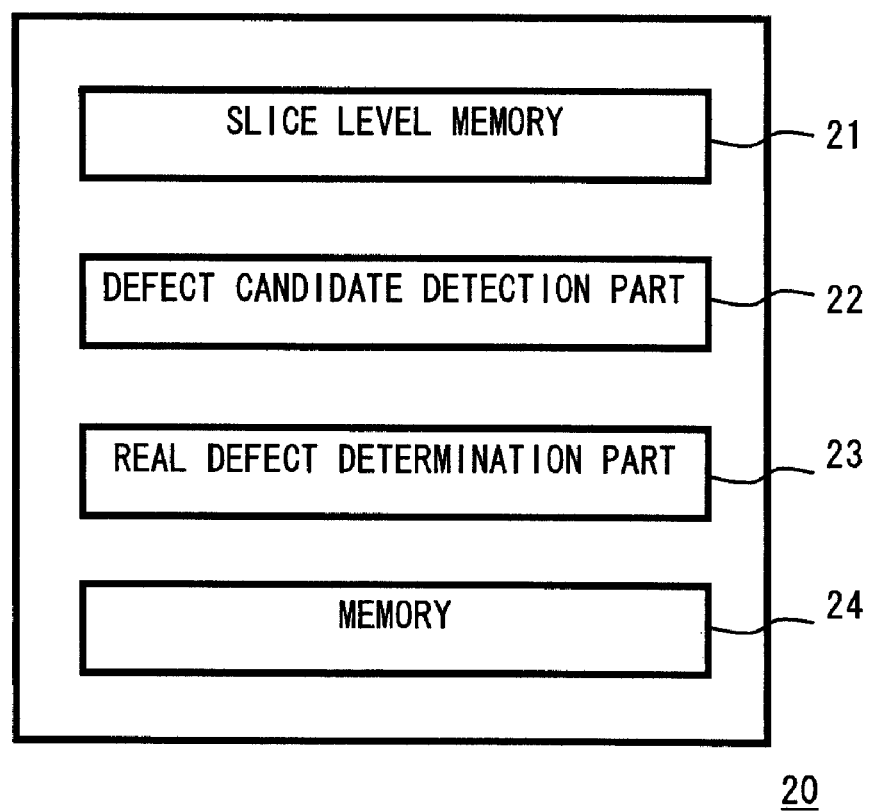
FIG. 2 shows a part of the configuration of the defect inspection apparatus according to the embodiment.

A defect inspection apparatus according to the present embodiments of the invention is described with reference to FIGS. 1 and 2. FIG. 1 shows a configuration of a defect inspection apparatus 10 according to the present embodiment. FIG. 2 is a block diagram showing a configuration of a process apparatus 20 of the defect inspection apparatus 10 according to the present embodiment. As shown in FIG. 1, the defect inspection apparatus 10 according to the present embodiment includes a laser source 11, a half mirror 12, an objective lens 13, a stage 14, a prism 15, a relay lens 16, a photodetector 17, a spatial filter 18, a scanner 19, and a process apparatus 20. In the present embodiment, the defect inspection apparatus 10 includes a confocal optical system and performs inspection of defect D using a reflected light of a sample W surface.

A light beam emitted from the laser source 11 is made incident on the half mirror 12. Each light beam is substantially parallel with each other. The half of the light beam is transmitted through the half mirror 12 to be made incident on the objective lens 13. The light beam which is made incident on the objective lens 13 is focused in appropriate spot diameter to be made incident on a sample W that is provided on the stage 14. The beam which is made incident on the sample W is reflected from its surface. The reflected beam is transmitted through the objective lens 13 to be light beam which is substantially parallel with each other. The light beam which is substantially parallel is separated from the light beam which is made incident on the sample W by the half mirror 12. Therefore, the half of the light beam is reflected in the direction of the photodetector 17.

The beam reflected from the half mirror 12 is made incident on the photodetector 17 through the relay lens 16. In the present embodiment, the prism 15 is provided in the optical path between the half mirror 12 and the relay lens 16. The prism 15 divides the light beam into two beams. As shown in FIG. 1, the shape of the prism 15 according to the present embodiment is such that two parallelogram prisms are united. The prism 15 is provided to be symmetric to the optical axis of the light beam reflected to the photodetector 17 side by the half mirror 12. Therefore, about half of the light beams reflected to the photodetector 17 side by the half mirror 12 is made incident on an upper half of the prism 15, and about half of them is made incident on a lower half of the prism 15. The beam which is made incident on the upper half of the prism 15 and the beam which is made incident on the lower half of the prism 15 have different angle in the incident surface of the prism 15, which means that the two beams are emitted in a different direction. The beam which is made incident on the upper half of the prism 15 is made incident on a light receiving element 17a through a pin hole 18a provided in the spatial filter 18. On the other hand, the beam which is made incident on the lower half of the prism 15 is made incident on a light receiving element 17b through a pin hole 18b provided in the spatial filter.

The detection by the confocal optical system can be easily performed by providing the spatial filter 18. Therefore, the beam reflected from the surface of the sample W which is provided in the focal position of the objective lens 13 can pass through the pin holes 18a and 18b, while the beam reflected from the surface deviated from the focal position cannot pass through the pin holes 18a and 18b. Therefore, the detection can be made by the confocal optical system and defect inspection with high accuracy can be performed by providing an image before the photodetector 17 and disposing the pin holes at the imaging point. The distance or space between the light receiving element 17a and the light receiving element 17b is such that the beam passed through the prism 15 can be separated.

Note that the shape of the prism 15 is not limited to the above description. For example, a wedge-shaped wedge prism may be provided at a substantially half position of the light beam reflected to the photodetector 17 side by the half mirror 12. In summary, the wedge prism having different angles of the incident surface and emit surface may be provided at the substantially half position of the light beam, which causes the beam incident on the wedge prism to be emitted in different directions. On the other hand, the beam which is not made incident on the wedge prism is emitted with keeping the lower direction. It is also possible to use a knife edge prism which reflects the incident beam in two divided beams. Further, it is possible to tilt the angles of the incident surface and the emit surface of the wedge to each side to obliquely emit the emit beam. The wedge may not be provided at the position that is substantially half of the optical path. The two wedges having different emit angles or one prism having the equivalent function may be provided on the optical path. Even in this case, substantially the same effect can be obtained. The edge part shape of the wedge may not be straight at the cross sectional surface of the optical path. The number of beams divided at the prism 15 is not limited to two but may be four or the like.

The output signals are output based on the intensities of the light beams detected at the light receiving elements 17a and 17b. Then the inspection of the surface state of the sample W is performed. In the present embodiment, the light beam scans the sample W with the scanner 19, and the stage 14 is two-dimensionally driven in a direction orthogonal to the scan direction of the light beam. The relative position between the sample W and the light spot is scanned along the scan line, and the whole surface of the sample W is inspected. For example, the scanner 19 of the light beam may be a vibration mirror such as a galvano mirror or polygon mirror or the like.

The scanning is performed so that the light spot focused on the sample W illuminates the region where the light spot overlaps the light spot of the adjacent scan line. It is determined that the defect detected by the adjacent light spot is the real defect, which makes it possible to detect defects with high accuracy. Note that the scan part of the light spot is not limited to the above-described example. For example, it is possible to drive only the stage 14 to perform inspection of the whole sample surface by raster scan. Further, the stage 14 may be rotary driven to perform inspection on the whole sample surface by spiral scan.

Figure 14:
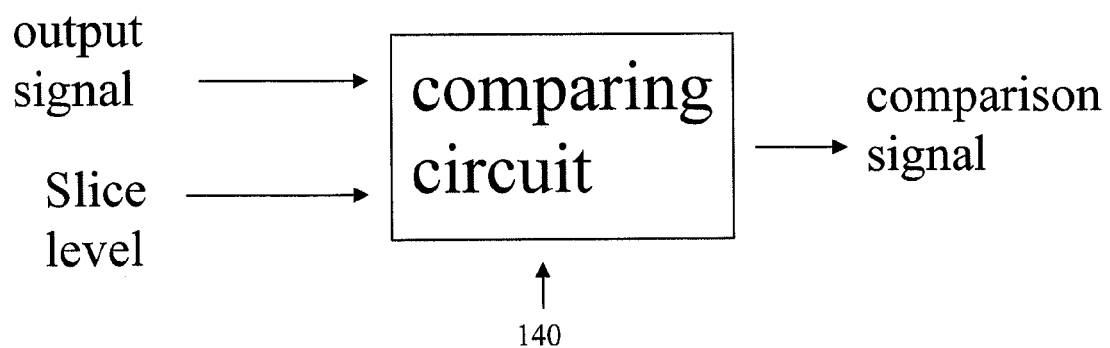
FIG. 14 shows an example of a comparing circuit.

The output signals from the photodetector 17 are transmitted to a process apparatus 20. As shown in FIG. 2, the process apparatus 20 includes a slice level memory 21, a defect candidate detection part 22, a real defect determination part 23, and a memory 24. In the slice level memory 21, positive slice level H and negative slice level L are set. The output signals from the photodetector 17 are compared with the slice level stored in the slice level memory 21 at the defect candidate detection part 22, and the signal exceeding the slice level is detected as the defect candidate. In other words, a pulse signal is output when the output signals are below the negative slice level L or when the output signals are below the slice level L. On the other hand, the pulse signal is output when the output signals are above the positive slice level H or when the output signals are above the slice level H. FIG. 14 illustrates comparing circuit 140. The detected defect candidate is determined by the real defect determination part 23 whether or not the defect candidate is real defect. The process of the real defect determination part 23 will be described later in detail. The position of the real defect on the sample W is determined by the positions of the light beam and the stage 14, and the obtained position is stored in the memory 24.

Figure 3:
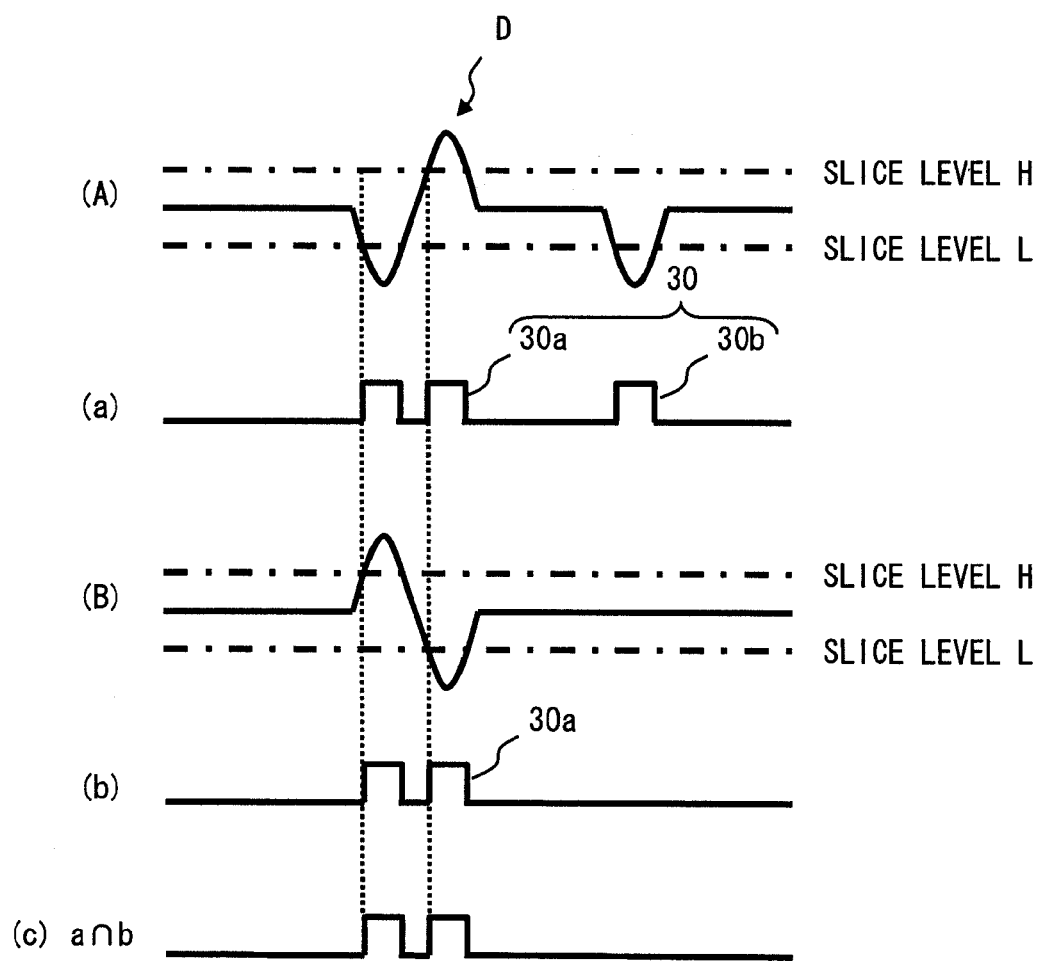
FIG. 3 shows an example of a detection signal in defect detection.

Referring now to FIG. 3, the detection of the reflected beam using the prism 15 will be described. FIG. 3 shows one example of the detection signal in defect detection. In FIG. 3, (A) shows the output signal from the light receiving element 17a and (B) shows the output signal from the light receiving element 17b. (a) shows the defect candidate signal based on the output signal from the light receiving element 17a and (b) shows the defect candidate signal based on the output signal from the light receiving element 17b. The light intensities of the light receiving element 17a and the light receiving element 17b are the same when the normal area having no defect is inspected. Therefore, the output signal from the light receiving element 17a and the output signal from the light receiving element 17b are the same.

Now, description will be made on a case where a convex defect D is inspected. When the stage 14 having the sample W thereon moves in a direction indicated in arrow in FIG. 1 and the laser beam is illuminated on the convex defect D, the laser beam first approaches an ascending slope. When the stage 14 moves and the laser beam passes through an apex of the convex defect D, the laser beam is illuminated on a descending slope. When the laser beam is illuminated on the ascending and descending slopes, the reflection angle of the laser beam is changed. More specifically, when the laser beam is illuminated on the ascending slope, the laser beam is shifted to the lower part of the prism 15. In other words, as shown in (A) in FIG. 3, the output signal output from the light receiving element 17a decreases to exceed the slice level L. On the other hand, the output signal output from the light receiving element 17b increases as shown in (B) in FIG. 3 to exceed the slice level H.

On the other hand, when the laser beam is illuminated on the descending slope, the laser beam is shifted to the upper part of the prism 15. As shown in (A) in FIG. 3, the output signal output from the light receiving element 17a increases to exceed the slice level H. On the other hand, the output signal output from the light receiving element 17b decreases as shown in (B) in FIG. 3 to exceed the slice level L. Therefore, when the convex defect D is inspected, the output signal of the light receiving element 17a is changed from the negative value to the positive value. The output signal of the light receiving element 17b is changed from the positive value to the negative value. The convex defect and the concave defect can be detected based on the change of the signal intensities of the light receiving element 17a and the light receiving element 17b.

Note that the prism 15 is preferably provided in a direction corresponding to the scan direction of the stage 14. It is possible to perform an inspection with high accuracy by providing the prism 15 in the direction to which the optical path is geometrically-optically tilted by the concave and convex defects in scanning the laser beam.

The area where the output signals exceed the slice level is detected as the defect candidate 30 by the defect candidate detection part 22. The area which is not a real defect but exceeds the slice level due to the noise or the like may also be detected as the defect candidate 30. In (a) in FIG. 3, the defect candidate 30a is the real defect whereas the defect candidate 30b is a false detection defect having no real defect.

When the slice levels are set both in upper side and lower side as in the present embodiment, there are two areas exceeding the slice level in one convex defect D when the defect candidate is detected from the output signals. In summary, two defect candidates 30a are detected by one convex defect D. When there are two areas exceeding the slice level in a certain distance in one scan line as in this case, these areas may be collectively regarded as one defect candidate.

Then it is determined in the real defect determination part 23 whether the detected defect is the real defect based on the defect candidate signal. More specifically, a determination signal obtained by extracting the same elements included in the defect candidate signals (a) and (b) in FIG. 3 is calculated in the real defect determination part 23 (a∩b shown in (c) in FIG. 3). In other words, the determination signal is 1 when both of the defect candidate signals based on the output signals output from the light receiving element 17a and the light receiving element 17b are 1. When the output signals output from the light receiving element 17a and the light receiving element 17b are detected substantially at the same time, the determination signal is 1. When the determination signal indicates 1, the defect candidate 30a is determined to be the real defect. The position of the defect candidate 30a which is the real defect is calculated from the position of the stage 14 and the illumination position of the light spot or the like, and the calculated position is stored in the memory 24.

On the other hand, 1 is detected in the defect candidate signal generated based on the output signal from the light receiving element 17a as shown in the defect candidate 30b, whereas 0 is detected in the defect candidate signal generated based on the output signal from the light receiving element 17b. Therefore, the determination signal a∩b which is obtained by extracting the same element included in the defect candidate signals (a) and (b) is 0. In this case, it is determined that the defect candidate 30b is the false defect.

Note that the output signal output from the light receiving element 17a and the output signal output from the light receiving element 17b may actually not be detected substantially at the same time due to the effect of the jitter, which is a swing of a time axis of the pulse of the defect candidate signal. Therefore, it is possible to determine the detected defect as the real defect when the output signals from the both light receiving elements 17a and 17b are detected within a certain period of time, in addition to the case where the output signals output from the light receiving element 17a and the light receiving element 17b are detected substantially at the same time. Hence, it is possible to detect the real defect with high sensitivity. The time determining the real defect is determined so as not to fail to detect the real defect in consideration of the jitter or the like.

Figure 4:
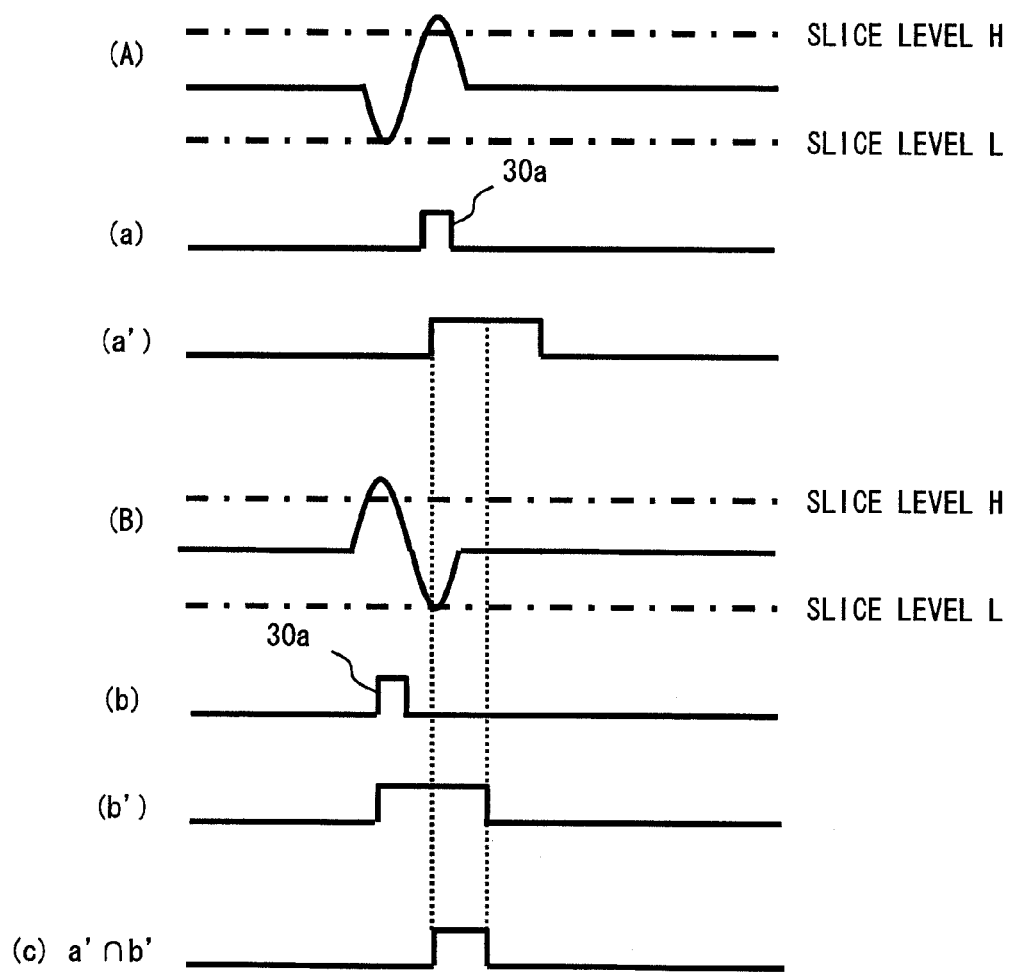
FIG. 4 shows another example of the detection signal in defect detection.
Figure 15:
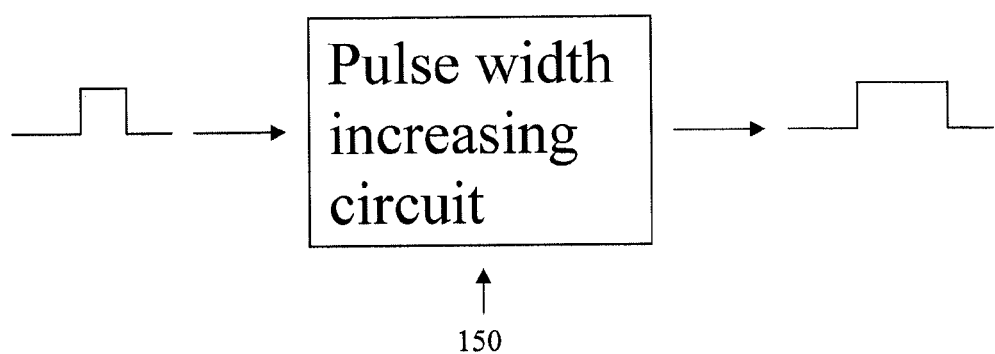
FIG. 15 shows an example of a pulse width increasing circuit.

Further, there may be a case where the intensity of the beam incident on the defect is fluctuated by the noise or the like, which causes the output signal to be top/bottom asymmetric. This case will now be described with reference to FIG. 4. FIG. 4 shows another example of the detection signal in defect detection. In FIG. 4, (A) shows the output signal from the light receiving element 17a and (B) shows the output signal from the light receiving element 17b. (a) shows the defect candidate signal based on the output signal from the light receiving element 17a and (b) shows the defect candidate signal based on the output signal from the light receiving element 17b. (a') shows the signal obtained by increasing pulse width of the defect candidate signal based on the output signal from the light receiving element 17a and (b') shows the signal obtained by increasing pulse width of the defect candidate signal based on the output signal from the light receiving element 17b. FIG. 15 illustrates an example of a pulse width increasing circuit 150.

As stated in FIG. 3, the light intensities of the light receiving element 17a and the light receiving element 17b are the same when the normal area having no defect is inspected. Therefore, the output signal from the light receiving element 17a and the output signal from the light receiving element 17b are the same. When the laser beam is illustrated on the convex defect D, the output signal output from the light receiving element 17a decreases as shown in (A) in FIG. 4 when the laser beam is illuminated on the ascending slope. On the other hand, the output signal output from the light receiving element 17b increases as shown in (B) in FIG. 4. On the contrary, the output signal output from the light receiving element 17a increases as shown in (A) in FIG. 4 when the laser beam is illuminated on the descending slope. On the other hand, the output signal output from the light receiving element 17b decreases as shown in (B) in FIG. 4.

However, in the case shown in FIG. 4, output signals from the light receiving elements 17a and 17b do not exceed the slice level L due to the noise. Therefore, the defect candidate signals (shown in (a) and (b) in FIG. 4) based on the output signals are not detected substantially at the same time. In such a case, the pulse widths of both defect candidate signals are increased. Therefore, the pulse width of the defect candidate signal shown in (a) in FIG. 4 is increased as shown in (a'), and the pulse width of the defect candidate signal shown in (b) in FIG. 4 is increased as shown in (b').

Then it is determined in the real defect determination part 23 whether or not the detected defect is the real defect based on the defect candidate signal whose pulse width is thus increased. More specifically, a determination signal obtained by extracting the same elements included in the defect candidate signals (a') and (b') in FIG. 4 is calculated in the real defect determination part 23 (a'∩b' shown in (c) in FIG. 4). The determination signal is 1 when both of the defect candidate signals based on the output signals output from the light receiving element 17a and the light receiving element 17b are 1. When the signal obtained by increasing pulse width of the output signal output from the light receiving element 17a and the signal obtained by increasing pulse width of the output signal output from the light receiving element 17b are detected substantially at the same time, the determination signal indicates 1. When the determination signal indicates 1, it is determined that the defect candidate 30a is the real defect. As stated above, it is possible to detect the real defect with higher sensitivity by increasing the pulse width of the defect candidate signal.

Figure 5:
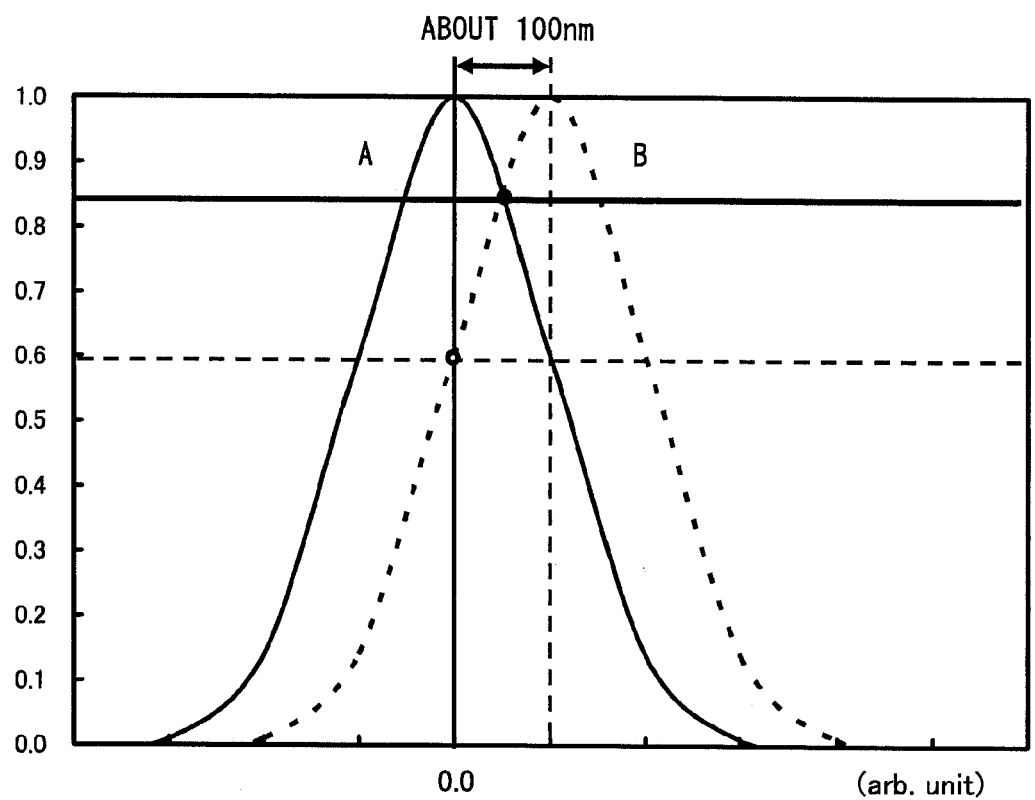
FIG. 5 shows an example of a beam profile of a light beam according to the embodiment.
Figure 6:
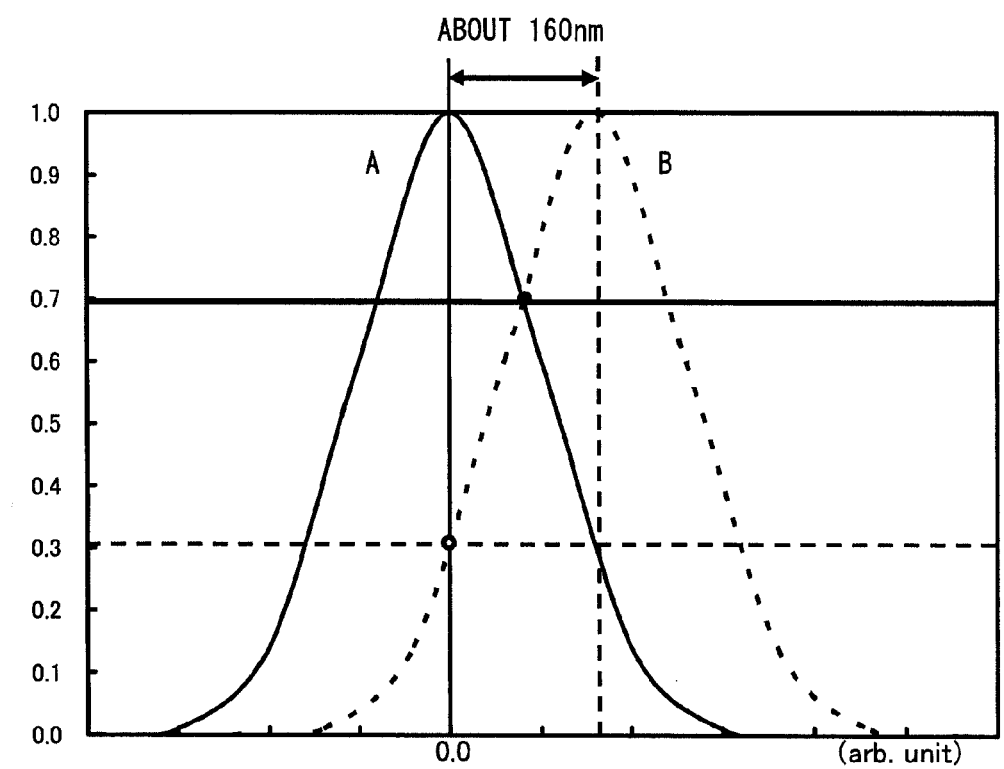
FIG. 6 shows another example of the beam profile of the light beam according to the embodiment.
Figure 7:
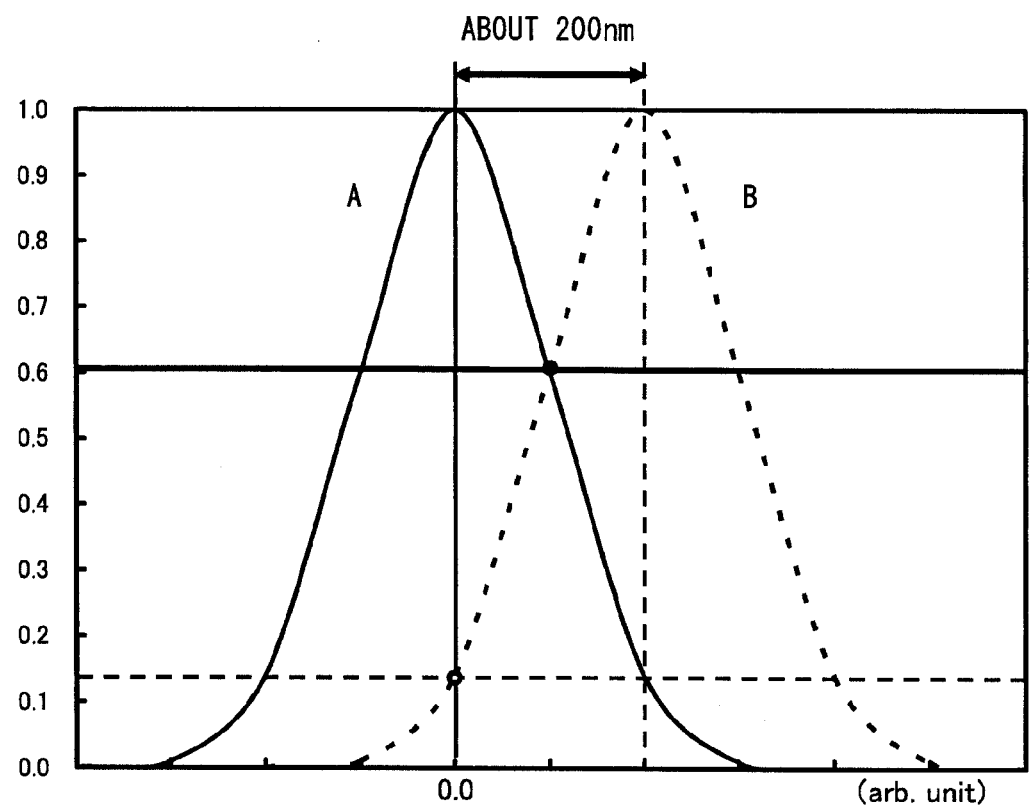
FIG. 7 shows another example of the beam profile of the light beam according to the embodiment.
Figure 8:
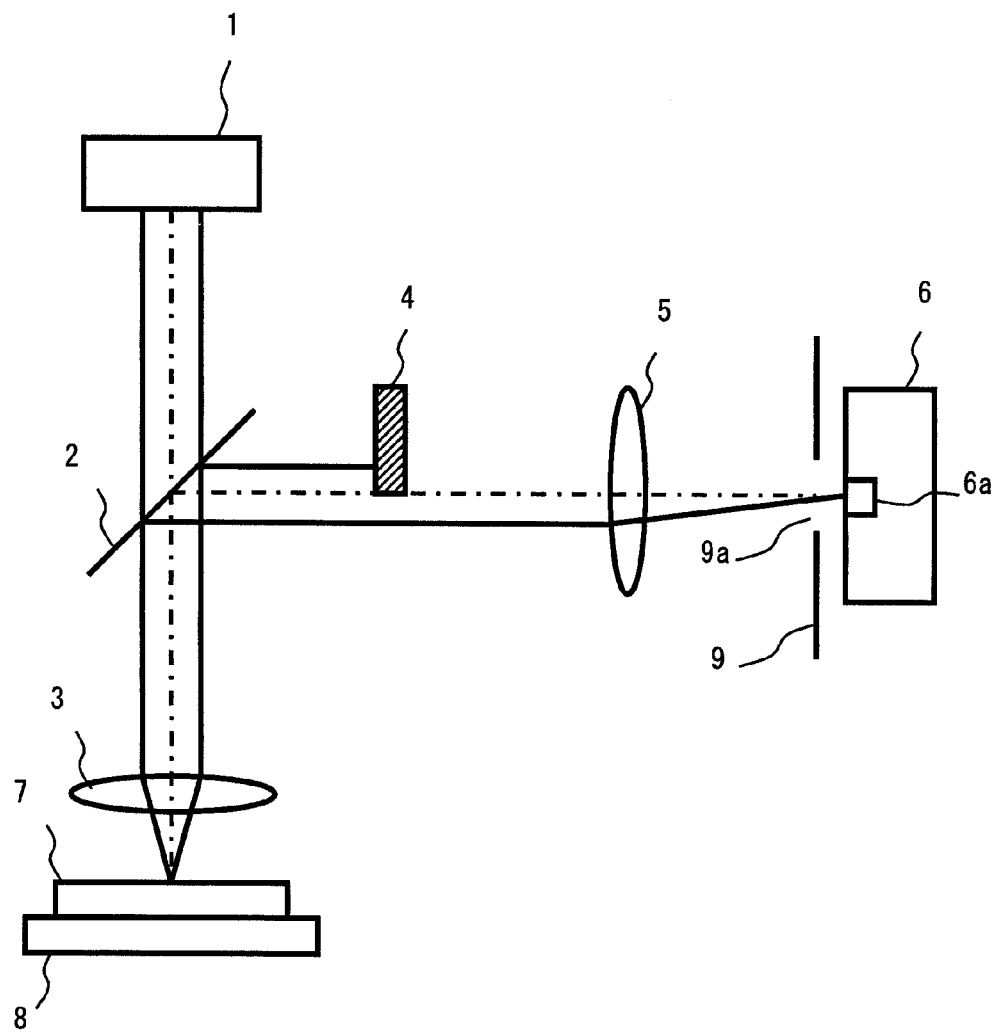
FIG. 8 shows a configuration of a conventional defect inspection apparatus.
Figure 9:
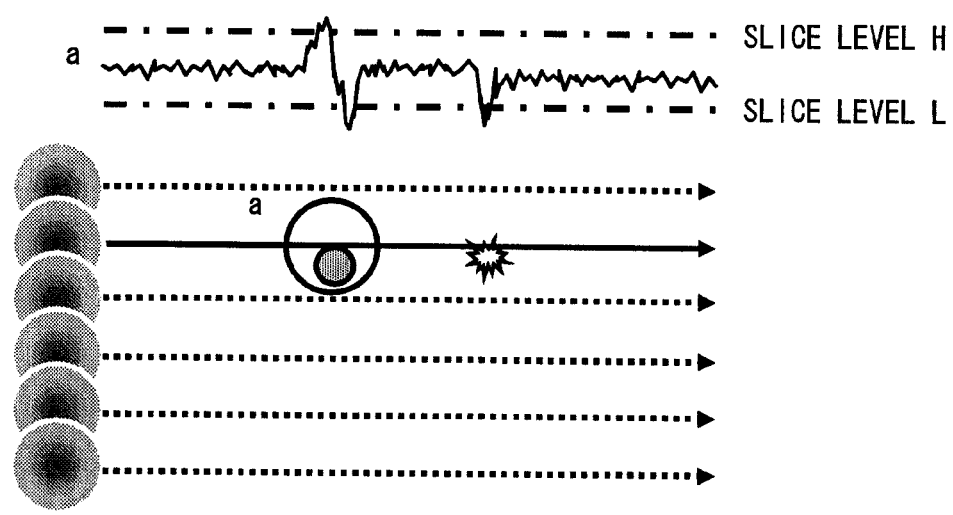
FIGS. 9 to 11 each shows a conventional example of the detection signal in defect detection.
Figure 10:
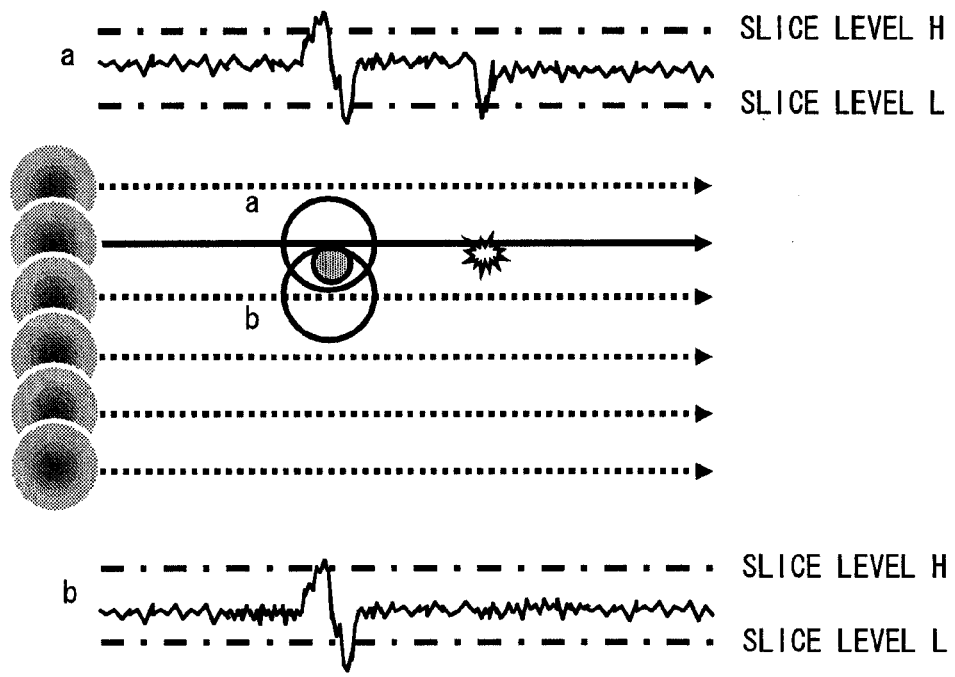
Figure 11:
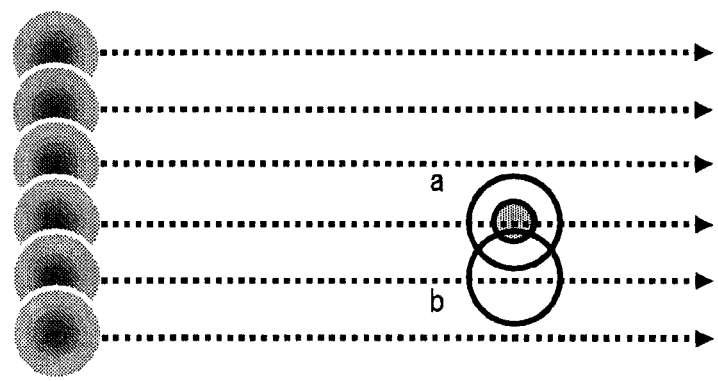

FIGS. 5 to 7 each shows a beam profile of the laser source 11 used in the present embodiment. As shown in FIGS. 5 to 7, the beam profile of the laser source 11 used in the present embodiment shows a normal distribution characteristic having a peak at the center thereof. Therefore, as the position of the defect is away from the center of the light spot illuminated on the sample W, the detection sensitivity of the defect decreases. In FIGS. 5 to 7, the light spot B having a beam profile shown in dashed line B is the light spot of the scan line which is adjacent to the light spot A shown in full line A. Therefore, light spot B is scanned so as to illuminate the region overlapping the light spot A of the adjacent scan line. In FIG. 5, the moving speed of the stage 14 is adjusted to be 1.0 as a reference. In FIG. 6, the moving speed of the stage 14 is adjusted to be 1.6. In FIG. 7, the moving speed of the stage 14 is adjusted to be 2.0.

In the example shown in FIG. 5, the light spot B is illuminated on a position about 100 nm away from the center of the light spot A of the adjacent scan line, which means the beam pitch is about 100 nm. In the conventional inspection apparatus where the light spot B focused on the sample scans the region where the light spot B overlaps the light spot A of the adjacent scan line so as to illuminate the region, the defect can be detected with high sensitivity in the light spot A when the defect in the position of 0.0 which is the center of the light spot A is detected. On the other hand, in the adjacent spot B, the beam intensity is low and the detection sensitivity is reduced as shown in open circle in FIG. 5.

Further, in an example shown in FIG. 6, the light spot B is illuminated on a position about 160 nm away from the center of the light spot A of the adjacent scan line, which means the beam pitch is about 160 nm. In an example shown in FIG. 7, the light spot B is illuminated on a position about 200 nm away from the center of the light spot A of the adjacent scan line, which means the beam pitch is about 200 nm. As is the same as the example shown in FIG. 5, in the conventional inspection apparatus, the defect can be detected with high sensitivity in the light spot A when the defect in the position of 0.0 which is the center of the light spot A is detected. On the other hand, in the adjacent spot B, the beam intensity is low and the detection sensitivity is reduced as shown in open circles in FIGS. 6 and 7.

The time required for inspection of the sample W is about 90 minutes in FIG. 5, about 56 minutes in FIG. 6, and about 45 minutes in FIG. 7. Although the time required for defect inspection can be shortened if the stage speed is made faster, the detection sensitivity and the detection accuracy are degraded as the stage speed is made faster.

However, in the present invention, the light blocking plate is not provided on the optical path. One light beam is divided into two light beams to detect defect using both of the two divided light beams. Therefore, it is possible to reduce loss of the signal intensity to detect the defect with high sensitivity. Further, one light beam is divided into two light beams, and it is determined that there is a real defect when the two light receiving elements detect the defect substantially at the same time. Therefore, one light beam and the other light beam are obtained by reflecting a part of one light spot focused on the surface of the sample W. In other words, the beam pitch in the inspection apparatus according to the present invention is substantially half of the beam pitch in the conventional inspection apparatus that scans the overlapped region. Hence, as shown in bullets in FIGS. 5, 6, and 7, it is possible to increase the beam intensity and to improve the detection sensitivity compared with the conventional technique.

In summary, according to the present invention, it is possible to improve the inspection speed and to reduce the time required for the inspection when the detection sensitivity is made equal to the detection sensitivity of the conventional inspection apparatus where the adjacent light spot scans the overlapped region. It is possible to improve the detection sensitivity of the defect when the inspection speed is made equal to the inspection speed of the conventional inspection apparatus.

Figure 12:
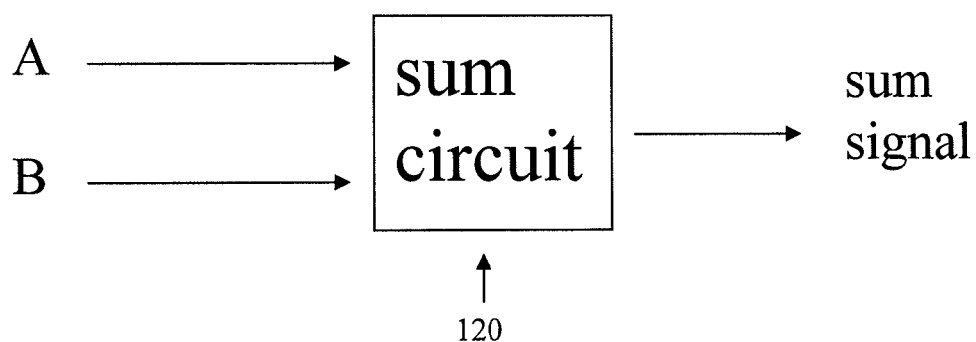
FIG. 12 shows an example of a sum circuit.
Figure 13:
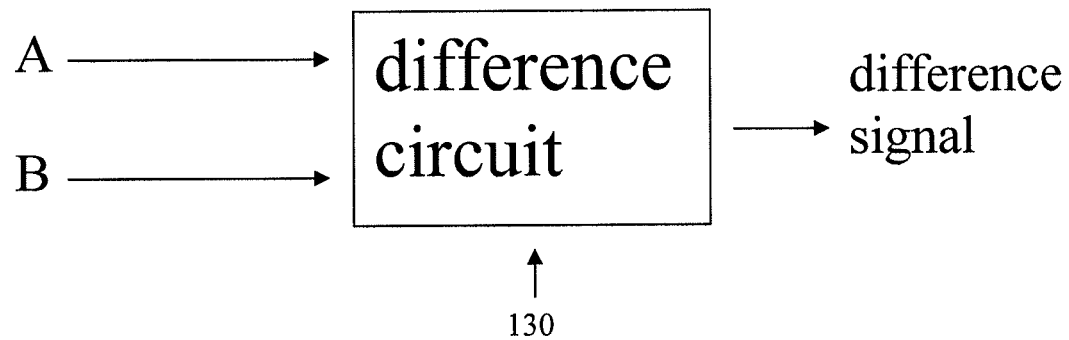
FIG. 13 shows an example of a difference circuit.

Note that it is preferable to use a method disclosed in Japanese Unexamined Patent Application Publication No. 2004-163198 in getting a detailed information of the defect using the signal detected by the photodetector. The type of the real defect is identified based on the difference signal or sum signal of the intensities of the output signals from the light receiving element 17*a* and the light receiving element 17*b*. The difference signal of the output signals of the light receiving elements 17*a* and 17*b* is the difference between (A) and (B) in FIG. 3. FIGS. 12 and 13 illustrate sum circuit 120 and difference circuit 130, respectively. Therefore, the difference signal has the signal waveform where the signal peak of (A) in FIG. 3 is enhanced. It is determined whether the defect on the sample W is the convex defect or the concave defect using the enhanced signal. As stated above, there are provided the slice level H and the slice level L. When the signal exceeds the slice level in an order of H to L, it is determined that the defect is the convex defect. The loss of the signal intensity of the difference signal is small since the signal of (A) in FIG. 3 is enhanced and it is therefore possible to perform the inspection with high accuracy and high precision.

In the present invention, the light blocking plate is not provided on the optical path, which reduces loss of the signal intensity and makes it possible to detect the defect with high S/N ratio. As stated above, the defect inspection apparatus according to the present invention is able to perform the inspection with high signal quality and with high accuracy and precision. The present invention is also effective in that a common noise such as a noise of the laser source 11 or the like can be effectively eliminated. Therefore, even when the intensity of the beam which is made incident on the defect fluctuates and the obtained signal is top/bottom asymmetric due to the noise or the like, it is possible to make a decision at the slice level with high accuracy.

When the concave defect is detected, the signals of (A) and (B) are changed to each other and the difference signal shows the behavior inverted from the convex defect. Therefore, when the signal exceeds the slice level in an order of L to H, it is determined that the defect is the concave defect. It can be determined whether the defect is the convex defect or the concave defect based on the order in which the signal exceeds the slice level. Hence, it is possible to determine whether the defect on the sample is the convex defect or the concave defect with high accuracy.

Further, when there is a spot-type defect on the sample surface, the output signal whose reflection ratio is partially changed is detected. In such a case, only a part of the reflection ratio of the sample surface is low, and the spot position of the laser beam is not changed and only the beam intensity is low. Therefore, both of the intensities of the output signals of the light receiving element 17*a* and the light receiving element 17*b* become low. Hence, the difference signal A−B is kept substantially 0. Therefore, in the difference signal, the signal does not exceed the slice levels H and L, which means the defect is not detected. In summary, when only a part of the reflection ratio of the sample surface is low, the signal of the A+B is enhanced. Therefore, when the sum signal A+B exceeds the slice level, it can be determined that this part is where only a part of the reflection ratio of the sample surface is low.

Further, if the slice level H is set and the A+B exceeds the slice level H, it can also be determined that this part is where the reflection ratio of the sample surface is partially high. This makes it possible to detect the spot-type defect. The sum signal is obtained by enhancing the output signals of the light receiving elements 17*a* and 17*b*. There is no light blocking plate on the optical path. Hence, it is possible to perform the inspection with high accuracy, with high precision, and with minimum loss of the signal intensity.

As stated above, according to the present invention, it is possible to reduce loss of the signal intensity and to detect the convex defect, the concave defect, and the spot-type defect with high S/N ratio. Then the inspection is made where in the sample W the defect exists and which type of defect exists by relating these defect detection signals to the position on the stage. According to the defect inspection apparatus of the present invention, it is possible to perform the inspection with high signal quality, with high accuracy, and with high precision. Note that the number of output signals is not limited to the examples of the present invention but the number may be any.

It is also possible to convert the light beam emitted from the laser source 11 into a plurality of light beams (multi beams) that are provided linearly or in matrix to illuminate the plurality of light beams on the sample W. It is also possible to provide a plurality of laser sources 11. Hence, it is possible to reduce time required for the inspection of the whole surface of the sample.

It is possible to improve manufacturing yield of the semiconductor device by manufacturing the pattern substrate with performing the defect inspection of the substrate by applying the inspection apparatus of the present invention to the inspection of the mask or mask blank or the inspection process of the semiconductor wafer. When the typical semiconductor device is manufactured, a mask original plate is set in the exposure apparatus, and the exposure process of the wafer having resist therein is executed using beam, ion beam, or electrical beam or the like. Then development process is executed on the semiconductor wafer after the exposure process, and the resist pattern is formed on the wafer. The pattern substrate is thus manufactured. According to the pattern, a widely-known thin-film deposition process, an etching process, an oxidation process, or an ion injection process or the like is performed so as to form the semiconductor device. By using a mask inspected by the inspection apparatus or the inspection method of the present invention or a mask using the mask blank, it is possible to perform the exposure process when the semiconductor device is manufactured. It is also possible to perform semiconductor device manufacturing process that is widely known on the wafer inspected by the inspection apparatus or the inspection method of the present invention so as to manufacture the semiconductor device.

In the present embodiment, the defect inspection apparatus includes a confocal optical system, and the defect is inspected by the reflected beam of the sample surface. However, it is also possible to perform the above-described defect inspection using a scattering beam in the sample surface or a transmission beam transmitting the sample.

Note that this invention is also applicable to other cases than defect inspection of the mask blank, the mask, the semiconductor device, and the semiconductor wafer. The optical system according to the present invention is applicable not only to the inspection apparatus of the defect, which is one of the sample states, but also to an optical scanning apparatus detecting general sample state such as microscope. The present invention is not limited to the examples as stated above but can be widely changed. For example, the same effect can be obtained by using wide variety of optical components or optical elements in addition to the optical system which is shown in the drawings.

From the invention thus described, it will be obvious that the embodiments of the invention may be varied in many ways. Such variations are not to be regarded as a departure from the spirit and scope of the invention, and all such modifications as would be obvious to one skilled in the art are intended for inclusion within the scope of the following claims.

What is claimed is:

1. An inspection apparatus comprising:
   a light source generating light beam;
   a lens focusing the light beam emitted from the light source to form a light spot on a sample surface;
   an optical dividing element dividing the light beam reflected from the sample surface or transmitted through the sample into a plurality of different light beams;
   a first photodetector receiving a first light beam divided by the optical dividing element to output a first output signal based on a beam amount of the received beam;
   a second photodetector receiving a second light beam divided by the optical dividing element to output a second output signal based on a beam amount of the received beam;
   a defect candidate detection part detecting a defect candidate based on the first output signal and the second output signal to output a first defect candidate signal and a second defect candidate signal; and
   a real defect determination part determining the defect candidate as a real defect upon detecting the first defect candidate signal and the second defect candidate signal within a certain period of time;
   wherein the optical dividing element is disposed at a position to divide the light beam substantially in half in a direction orthogonal to an optical axis of the light beam when the light beam is reflected from a region having no defects on the sample, and
   wherein the optical dividing element divides the light beam by changing a propagation direction of the light beam which is made incident on the optical dividing element into different propagation directions.

2. The inspection apparatus according to claim 1, wherein the real defect determination part determines that the defect candidate is the real defect when the first defect candidate signal and the second defect candidate signal are detected substantially at the same time.

3. The inspection apparatus according to claim 1, further comprising a circuit increasing pulse widths of the first defect candidate signal and the second defect candidate signal,
   wherein the real defect determination part determines that the defect candidate is the real defect when the first defect candidate signal and the second defect candidate signal whose pulse widths are increased are detected substantially at the same time.

4. The inspection apparatus according to claim 1, further comprising a scan part scanning relative positions of the sample and the light spot along a scan line,
   wherein the scan part scans a region where the light spot overlaps the light spot of an adjacent scan line so as to illuminate the region.

5. The inspection apparatus according to claim 1, wherein the optical dividing element is a prism disposed on the optical path of the light beam reflected from the sample.

6. The inspection apparatus according to claim 1, further comprising:
   a circuit calculating a difference signal based on the first output signal and the second output signal; and
   a first comparing circuit comparing the difference signal with a slice level,
   wherein a defect type of the sample is identified based on the comparing result of the first comparing circuit.

7. The inspection apparatus according to claim 1, further comprising:
   a circuit calculating a sum signal based on the first output signal and the second output signal; and
   a second comparing circuit comparing the sum signal with a slice level,
   wherein a defect type of the sample is identified based on the comparing result of the second comparing circuit.

8. The inspection apparatus according to claim 1, wherein the light beam emitted from the light source is converted into a plurality of light beams.

9. The inspection apparatus according to claim 1, wherein the inspection apparatus includes a plurality of light sources.

10. An inspection method inspecting a defect of a sample using a light beam, comprising:
    a step for forming a light spot on a sample surface by focusing the light beam to illuminate the light spot on the sample;
    a step for relatively moving the light spot and the sample to scan the sample surface by the light spot;
    a step for dividing the light beam reflected from the sample surface or transmitted through the sample into a first light beam and a second light beam;
    a step for detecting a first defect candidate signal from a first output signal based on a beam amount of the first light beam;
    a step for detecting a second defect candidate signal from a second output signal based on a beam amount of the second light beam; and
    a step for determining a defect candidate as a real defect upon detecting the first defect candidate signal and the second defect candidate signal within a certain period of time;
    wherein the step for dividing the light beam reflected from the sample into the first light beam and second light beam comprises dividing the light beam substantially in half in a direction orthogonal to an optical axis of the light beam when the light beam is reflected from a region of the sample having no defects.

11. The inspection method according to claim 10, wherein the defect candidate is determined as the real defect when the first defect candidate signal and the second defect candidate signal are detected substantially at the same time.

12. The inspection method according to claim 10, comprising a step for increasing pulse widths of the first defect candidate signal and the second defect candidate signal,
    wherein the defect candidate is determined as the real defect when the first defect candidate signal and the second defect candidate signal whose pulse widths are increased are detected substantially at the same time.

13. The inspection method according to claim 10, comprising a step for scanning a region where the light spot overlaps the light spot of an adjacent scan line so as to illuminate the region.

14. The inspection method according to claim 10 comprising:
   a step for calculating a difference signal based on the first output signal and the second output signal; and
   a step for comparing the difference signal with a slice level to identify a defect type of the sample based on the comparing result.

15. The inspection method according to claim 10 comprising:
   a step for calculating a sum signal based on the first output signal and the second output signal; and
   a step for comparing the sum signal with a slice level to identify a defect type of the sample based on the comparing result.

16. A manufacturing method of a pattern substrate comprising:
   a step for detecting a defect of a substrate using the inspection method according to claim 10, the substrate being a sample;
   a step for modifying the detected defect; and
   a step for forming a pattern on the substrate whose defect is modified.

* * * * *